(12) United States Patent
Taguchi et al.

(10) Patent No.: US 7,535,992 B2
(45) Date of Patent: May 19, 2009

(54) X-RAY DIFFRACTION APPARATUS

(75) Inventors: Takeyoshi Taguchi, Tachikawa (JP); Masaru Kuribayashi, Akishima (JP)

(73) Assignee: Rigaku Corporation, Tokyo (JP)

( * ) Notice: Subject to any disclaimer, the term of this patent is extended or adjusted under 35 U.S.C. 154(b) by 20 days.

(21) Appl. No.: 11/477,188

(22) Filed: Jun. 28, 2006

(65) Prior Publication Data
US 2007/0003012 A1 Jan. 4, 2007

(30) Foreign Application Priority Data
Jun. 30, 2005 (JP) ............................. 2005-191046

(51) Int. Cl.
*H01J 35/08* (2006.01)
(52) U.S. Cl. ........................................ 378/124; 378/71
(58) Field of Classification Search .................... 378/71, 378/73, 75, 124, 147, 149
See application file for complete search history.

(56) References Cited

U.S. PATENT DOCUMENTS

| 2,549,987 | A | * | 4/1951 | Hamacher et al. .............. 378/73 |
| 7,145,983 | B2 |  | 12/2006 | Taguchi et al. |
| 2002/0053641 | A1 | * | 5/2002 | Verbruggen ............ 250/370.09 |
| 2003/0156682 | A1 | * | 8/2003 | Yokhin et al. ................. 378/70 |
| 2004/0136499 | A1 | * | 7/2004 | Holland et al. .............. 378/119 |
| 2005/0058247 | A1 |  | 3/2005 | Taguchi et al. |

FOREIGN PATENT DOCUMENTS

| JP | 09-068507 | A | 3/1997 |
| JP | 11-304728 | A | 11/1999 |
| JP | 2005-091142 | A | 4/2005 |

OTHER PUBLICATIONS

Japanese Office Action (and Summarized English Translation thereof) dated Jun. 5, 2007, issued in a counterpart Japanese Application.

* cited by examiner

*Primary Examiner*—Edward J Glick
*Assistant Examiner*—Mona M Sanei
(74) *Attorney, Agent, or Firm*—Frishauf, Holtz, Goodman & Chick, P.C.

(57) ABSTRACT

An X-ray diffraction apparatus allows plural kinds of characteristic X-rays to be incident on a sample at the same time and thus allows X-ray diffraction measurement with the plural kinds of characteristic X-rays to be carried out at the same time. An X-ray tube includes an anode which has the first target region made of Co and the second target region made of Cu. The first and second target regions are sectioned in a direction (Z-direction) perpendicular to an X-ray take-off direction. Incident-side and receiving-side Z-direction-divergence restriction devices restrict the X-ray divergence in the Z-direction. An X-ray detector is position sensitive at least in the Z-direction and can detect separately a diffracted X-ray coming from the first sample region which is irradiated with the Co characteristic X-ray and another diffracted X-ray coming from the second sample region which is irradiated with the Cu characteristic X-ray. The detector may be a two-dimensional CCD sensor capable of executing a TDI operation.

5 Claims, 8 Drawing Sheets

FIG. 6

Channel number

|   | 1 | 2 | 3 | 4 | 5 | ... |
|---|---|---|---|---|---|---|
| 1 | S(1, 1) | S(2, 1) | S(3, 1) | S(4, 1) | S(5, 1) | |
| 2 | S(1, 2) | S(2, 2) | S(3, 2) | | | |
| 3 | S(1, 3) | S(2, 3) | | | | |
| 4 | S(1, 4) | | | | | |
| ⋮ | | | | | | |
| | | | | | | |
| | | | | | | |
| | | | | | | |
| | | | | | | |
| M | S(1, M) | S(2, M) | S(3, M) | S(4, M) | S(5, M) | |

M columns

↓ ↓ ↓ ↓ ↓

| T(1) | T(2) | T(3) | T(4) | T(5) | |
|---|---|---|---|---|---|

Sum of 1st to Mth columns

X-RAY DIFFRACTION APPARATUS

BACKGROUND OF THE INVENTION

1. Field of the Invention

The present invention relates to an X-ray diffraction apparatus allowing X-ray diffraction measurement of a sample to be carried out with the use of plural kinds of characteristic X-rays emitted by plural kinds of target materials.

2. Description of the Related Art

An X-ray diffraction apparatus allowing X-ray diffraction measurement of a sample to be carried out with the use of plural kinds of characteristic X-rays emitted by plural kinds of target materials is disclosed in Japanese patent publication No. 11-304728 A (1999) which is referred to as the first publication hereinafter. The first publication discloses, for a start, a rotating-anode X-ray tube which generates plural kinds of characteristic X-rays. The rotating-anode X-ray tube has two kinds of target regions made of Co (cobalt) and Cu (copper) respectively. Regarding how to arrange the two target regions, plural embodiments are disclosed, one of which is an arrangement in that Co and Cu are sectioned in a direction parallel to an axis of rotation of the rotating anode as shown in FIG. 3 of the present application. The upper part of the rotating anode emits the characteristic X-ray of Co, while the lower part emits the characteristic X-ray of Cu. The first publication further discloses X-ray diffraction measurement of a sample with the use of such two kinds of characteristic X-rays. That is, a monochromator is arranged between the X-ray tube and the sample, the monochromator consisting of an upper half having a multilayer film thereon allowing only the Co characteristic X-ray to be reflected and a lower half having another multilayer film thereon allowing only the Cu characteristic X-ray to be reflected. Between the sample and an X-ray detector is arranged a Soller slit for restricting the vertical divergence of X-ray. The X-ray detector is a scintillation counter. With a combination of the monochromator and the Soller slit, the Co characteristic X-ray passes through the upper half of the X-ray path almost in a parallel beam form, while the Cu characteristic X-ray passes through the lower half of the X-ray path almost in a parallel beam form. When intending to carry out X-ray diffraction measurement of the sample using the Co characteristic X-ray, the lower half of the X-ray path is shut off by a shutter which is arranged between the monochromator and the sample, so that only the Co characteristic X-ray is incident on the sample. On the other hand, when intending to carry out X-ray diffraction measurement of the sample using the Cu characteristic X-ray, the upper half of the X-ray path is shut off by the shutter, so that only the Cu characteristic X-ray is incident on the sample. Thus, the X-ray diffraction measurement of the sample using the two kinds of characteristic X-rays becomes possible.

Additionally, the present invention is also concerned with X-ray diffraction measurement of the sample using a position-sensitive X-ray detector. Electronic recording of a diffracted X-ray using the position-sensitive X-ray detector, specifically a two-dimensional CCD sensor, is disclosed in Japanese patent publication No. 2005-91142 A, which is referred to as the second publication hereinafter. The second publication discloses that a two-dimensional CCD sensor of the FFT (Full Frame Transfer) type is allowed to execute the TDI (Time Delay Integration) operation, making it possible to carry out high-speed, high-sensitive X-ray diffraction measurement.

As has been disclosed in the first publication, if using an X-ray tube which can emit two kinds of characteristic X-rays, it is possible to carry out X-ray diffraction measurement of a sample using the two kinds of characteristic X-rays. It is impossible, however, in the first publication to carry out X-ray diffraction measurement of a sample at the same time with the use of the two kinds of characteristic X-rays, because the shutter allows only any one of the characteristic X-ray to be incident on the sample. If the shutter is fully opened to allow the two kinds of characteristic X-rays to be incident on the sample at the same time, the scintillation counter will receive at the same time both the diffracted X-ray of the Co characteristic X-ray from the sample and the diffracted X-ray of the Cu characteristic X-ray from the sample, making it impossible to separately detect the two kinds of diffracted X-rays.

SUMMARY OF THE INVENTION

It is an object of the present invention to provide an X-ray diffraction apparatus which allows plural kinds of characteristic X-rays to be incident on a sample at the same time and can execute X-ray diffraction measurement using the plural kinds of characteristic X-rays at the same time.

An X-ray diffraction apparatus according the present invention allows plural kinds of characteristic X-rays to be incident on a sample so as to execute X-ray diffraction measurement of the sample, and comprises an X-ray tube, a sample holder, incident-side and receiving-side Z-direction-divergence restriction devices, and an X-ray detector which is position sensitive in a Z-direction. The X-ray tube includes an anode having a first target region made of a first material and a second target region made of a second material which is different from the first material. The first target region and the second target region are sectioned in a direction perpendicular to an X-ray take-off direction. The direction perpendicular to the X-ray take-off direction is defined as a Z-direction. The sample holder holds a sample so as to be irradiated with, at the same time, a first characteristic X-ray emitted from the first target region and a second characteristic X-ray emitted from the second target region. The incident-side Z-direction-divergence restriction device is arranged between the X-ray tube and the sample to restrict X-ray divergence in the Z-direction. The receiving-side Z-direction-divergence restriction device is arranged between the sample and the X-ray detector to restrict X-ray divergence in the Z-direction. The X-ray detector is position sensitive at least in the Z-direction and can detect separately a diffracted X-ray coming from a first region of sample which is irradiated with the first characteristic X-ray and another diffracted X-ray coming from a second region of sample which is irradiated with the second characteristic X-ray.

The X-ray detector may be a one-dimensional or two-dimensional X-ray detector which is position sensitive at least in the Z-direction, preferably a one-dimensional or two-dimensional CCD sensor such as a two-dimensional CCD sensor capable of executing a TDI operation.

The incident-side and the receiving-side Z-direction-divergence restriction devices each may be any device which can restrict narrower the Z-direction divergence angle such as a Soller slit. These Z-direction-divergence restriction devices may preferably restrict the Z-direction divergence angle to not greater than 0.5 degree for example.

The X-ray diffraction apparatus according to the present invention has an advantage that plural kinds of characteristic X-rays can be incident on a sample at the same time and X-ray diffraction measurement using the plural kinds of characteristic X-rays can be carried out at the same time.

BRIEF DESCRIPTION OF THE DRAWINGS

FIG. 6 illustrates an arrangement of storage cells of the CCD sensor;

DETAILED DESCRIPTION OF THE PREFERRED EMBODIMENTS

Figure 1:
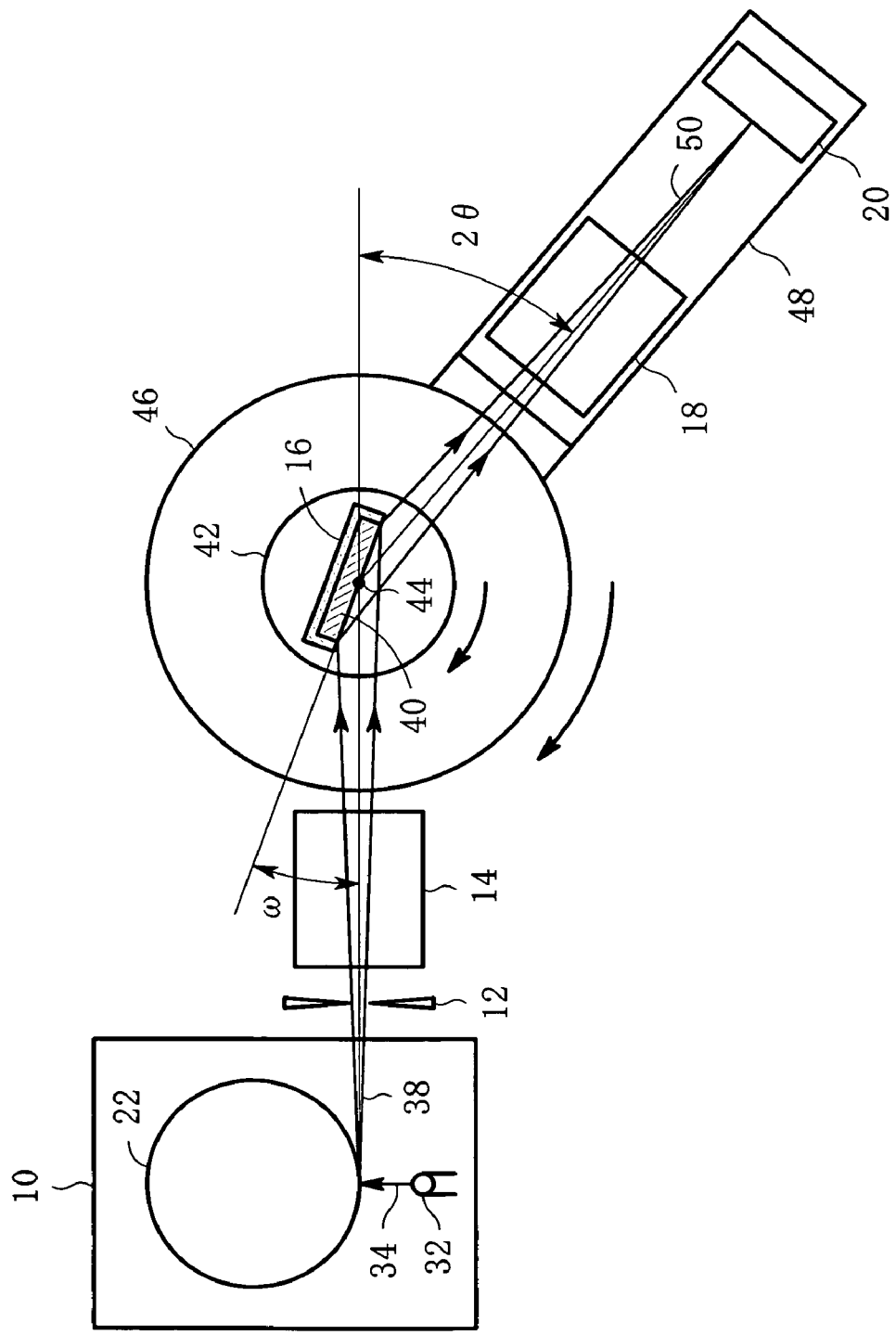
FIG. 1 is a plan view of one embodiment of an X-ray diffraction apparatus according to the present invention.
Figure 2:
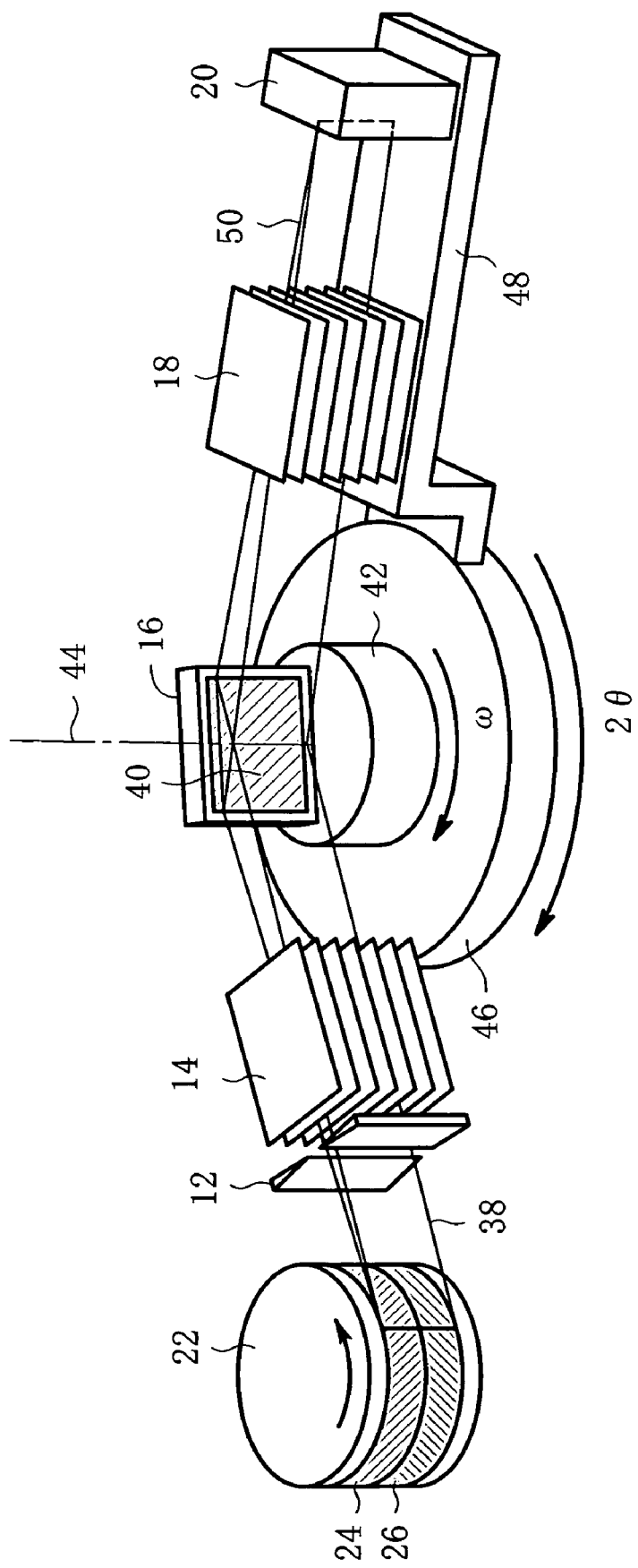
FIG. 2 is a perspective view of the X-ray diffraction apparatus shown in FIG. 1.

Embodiments of the present invention will now be described in detail below with reference to the drawings. FIG. 1 is a plan view of one embodiment of an X-ray diffraction apparatus according to the present invention, and FIG. 2 is a perspective view of the embodiment, noting that FIG. 2 shows only an anode for an X-ray tube. Referring to FIGS. 1 and 2, the X-ray diffraction apparatus has an X-ray tube 10, a divergence slit 12, an incident-side Soller slit 14, a sample holder 16, a receiving-side Soller slit 18 and an X-ray detector 20.

Figure 3:
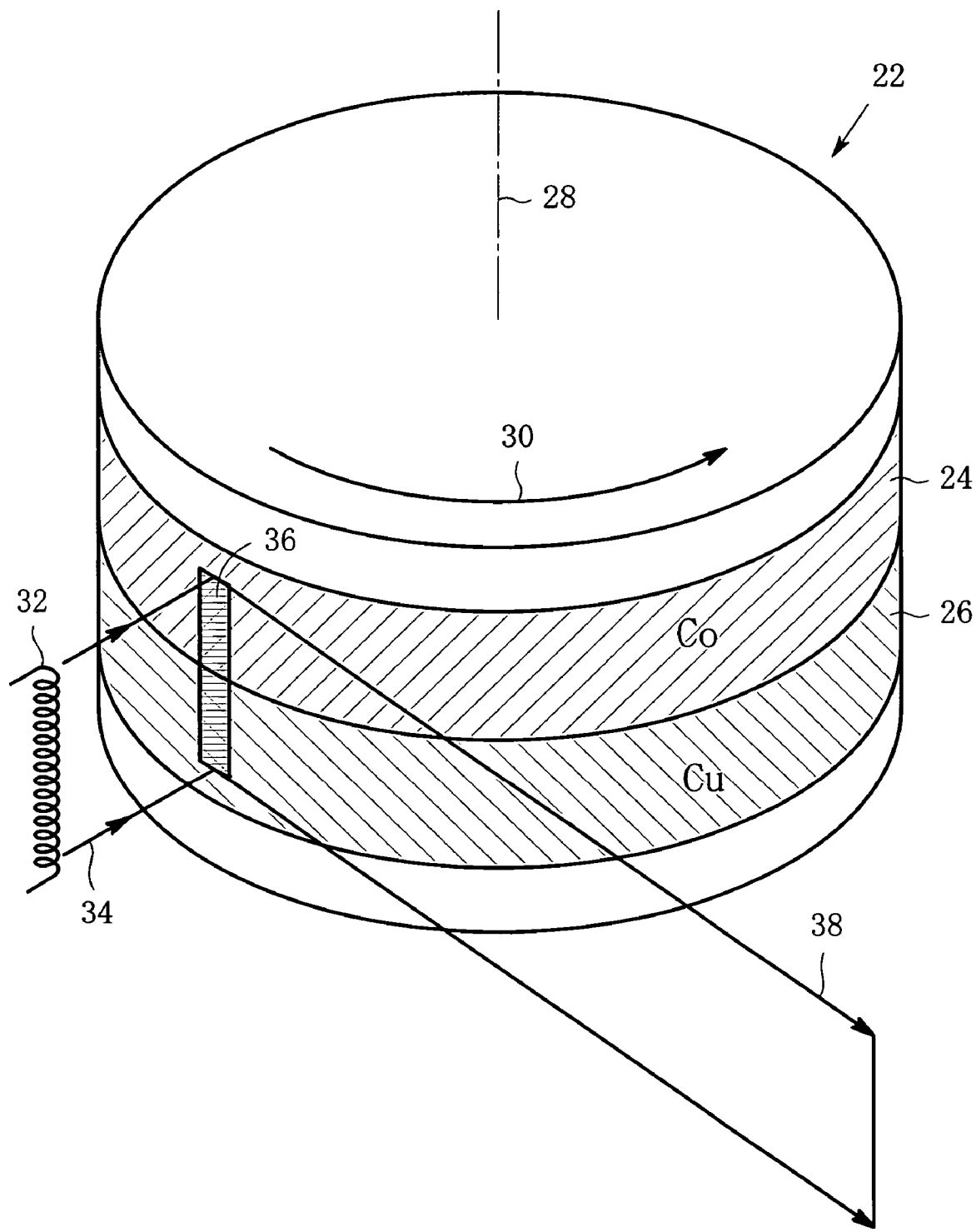
FIG. 3 is a perspective view of a rotating anode.

The X-ray tube 10 is a rotating-anode X-ray tube and its rotating anode 22 has, as shown in FIG. 3, the first target region 24 and the second target region 26. The first target region 24 is made of Co (cobalt), which is the first material, and has a ring shape. The second target region 26 is made of Cu (copper), which is the second material, and has a ring shape similarly. The two target regions 24 and 26 are sectioned in a direction parallel to an axis of rotation 28 of the rotating anode 22. Since the axis of rotation 28 of the rotating anode 22 extends vertically in this embodiment, the first target region 24 resides at the upper side while the second target region 26 resides at the lower side, the two target region being sectioned vertically. The two target regions 24 and 26 are about 5 mm in vertical size respectively for example. The rotating anode 22 rotates in a direction of an arrow 30. When an electron beam 34 from a cathode filament 32 is incident on the periphery of the rotating anode 22 which is revolving, one part of an electron beam irradiation region 36, which belongs to the first target region 24, emits the Co characteristic X-ray CoKα (the first characteristic X-ray) while the other part of the electron beam irradiation region 36, which belongs to the second target region 26, emits the Cu characteristic X-ray CuKα (the second characteristic X-ray). Therefore, the upper part of an X-ray beam 38 emitted from the rotating anode 22 is the Co characteristic X-ray while the lower part is the Cu characteristic X-ray, provided that the emitted X-rays travel in parallel with each other. Actually, since X-rays are emitted in various directions, the X-rays do not necessarily travel in parallel with each other. In the optical system of the X-ray diffraction apparatus, however, since the X-ray divergence angle is restricted narrower at least in the vertical direction as will be described below, the X-ray beam used for X-ray diffraction has a feature that the upper part of the beam is the Co characteristic X-ray while the lower part is the Cu characteristic X-ray as has been described above.

The take-off direction of the X-ray beam 38 depends on the positional relationship between the electron beam irradiation region 36 on the rotating anode 22 and a window of the X-ray tube, the take-off direction being horizontal in this embodiment. The two target regions 24 and 26 are sectioned in a direction perpendicular to such a take-off direction. Accordingly, the Z-direction in the present invention is a vertical direction in this embodiment.

Referring back to FIGS. 1 and 2, the sample holder 16 is formed with a recess which is filled with powdered sample 40. The sample holder 16 is arranged at a suitable position so that the sample 40 is irradiated with the two kinds of characteristic X-rays at the same time. The sample holder 16 is fixed to a sample turntable 42 which can rotate around an axis of rotation 44 of a goniometer. This rotation will be referred to as an ω-rotation and an angle between the X-ray beam 38 passing across the axis of rotation 44 and a surface of the sample 40 is defined as an angle ω. Further, there is also a 2θ turntable 46 which can rotate independently of the sample turntable 40. The 2θ turntable 46 also can rotate around the axis of rotation 44 and this rotation will be referred to as a 2θ-rotation. To the 2θ turntable 46 is fixed a detector arm 48 which is equipped with the receiving-side Soller slit 18 and the X-ray detector 20. An angle between the X-ray beam 38 passing across the axis of rotation 44 and a line (which corresponds to a direction of a diffracted X-ray 50) connecting the axis of rotation 44 and the center of the X-ray detector 20 is defined as an angle 2θ.

The divergence slit 12 is arranged between the X-ray tube 10 and the sample 40 and restricts a horizontal divergence angle (which is a divergence angle in the diffraction plane, i.e., a transverse divergence angle) of the X-ray beam 38 to a predetermined angle. The horizontal divergence angle is set to two degrees in the embodiment. The incident-side Soller slit 14 is arranged between the divergence slit 12 and the sample 40. The incident-side Soller slit 14 restricts a vertical divergence angle (which is a divergence angle in the direction perpendicular to the diffraction plane, i.e., a longitudinal divergence angle) of the X-ray beam 38 to a small angle. The vertical divergence angle is set to within 0.5 degree in the embodiment so as to collimate the X-ray beam 38 in the vertical direction. Thus, the upper half of the X-ray beam 38 which is incident on the sample 40 becomes only the Co characteristic X-ray while the lower half becomes only the Cu characteristic X-ray. The receiving-side Soller slit 18 restricts a vertical divergence angle of the diffracted X-ray 50 from the sample 40 to a small angle, the vertical divergence angle being set to within 0.5 degree in the embodiment so as to collimate the diffracted X-ray 50 in the vertical direction. Thus, the upper half of the diffracted X-ray 50 which enters the X-ray detector 20 becomes only the diffracted X-ray coming from the Co characteristic X-ray while the lower half becomes only the diffracted X-ray coming from the Cu characteristic X-ray. The incident-side Soller slit 14 corresponds to the incident-side Z-direction-divergence restriction device in the present invention, and the receiving-side Soller slit 18 corresponds to the receiving-side Z-direction-divergence restriction device in the present invention.

Figure 4:
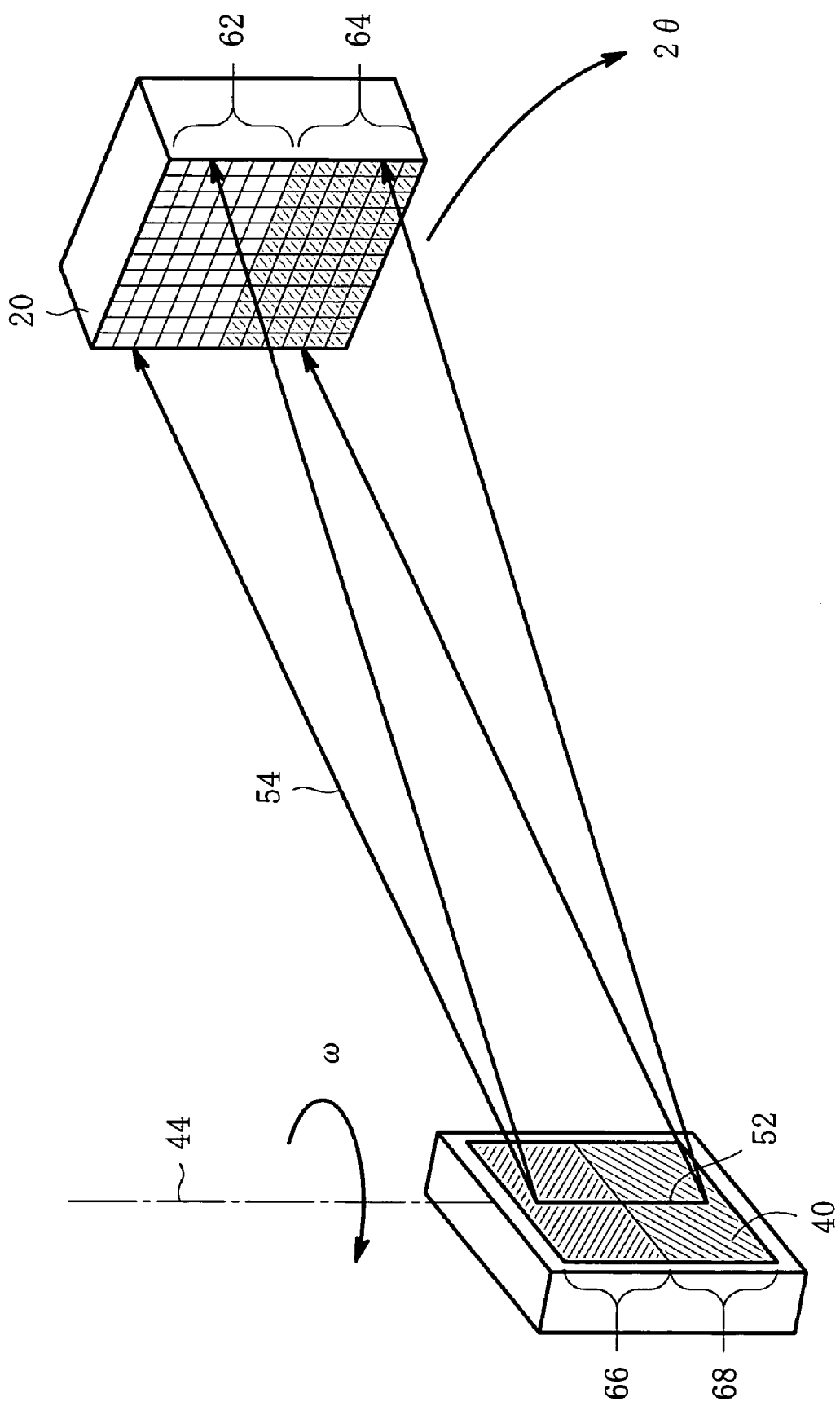
FIG. 4 is a perspective view showing a positional relationship between a sample and an X-ray detector.

Next, the X-ray detector 20 will be explained. The X-ray detector 20 is a two-dimensional CCD sensor capable of executing the TDI operation. FIG. 4 is a perspective view showing a positional relationship between the sample 40 and the X-ray detector 20. During the X-ray diffraction measurement, the sample 40 rotates with the ω-rotation around the axis of rotation 44 of the goniometer while the CCD sensor 20 rotates with the 2θ-rotation around the same axis of rotation 44. The sample 40 and the CCD sensor 20 are allowed to synchronously rotate with an angular velocity ratio of ω:2θ=1:2 so as to execute so-called θ/2θ scanning of a combination of the sample 40 and the CCD sensor 20. As shown in FIG. 1, a relatively wide area on the sample 40 is irradiated, with an incident angle ω, with the X-ray beam 38 having a predetermined horizontal divergence angle, and the diffracted X-ray 50 from the sample 40 is detected by the X-ray detector 20 residing at an angle 2θ which is two-fold of ω. Accordingly, the X-ray diffraction apparatus shown in FIG. 1 has fundamentally the focusing method optical system, with which powder diffraction patterns of the sample 40 can be recorded in the CCD sensor 20.

Referring to FIG. 4, considering a slender area 52 extending vertically on the sample 40, a diffracted X-ray 54 coming from the area 52 reaches the CCD sensor 20 which moves in the so-called θ/2θ scanning mode, the X-ray intensity on the CCD sensor 20 becoming highest near the horizontal center of the CCD sensor 20 and having a certain horizontal distribution centering on the highest part. When using the TDI-operable two-dimensional CCD sensor, such an X-ray intensity distribution is all recorded at the same time, that is to say, a part of the distribution which would be shut off and not detected in the ordinary focusing method can be recorded, so that high-speed, high-sensitive measurement is possible.

The first region 66 which is the upper half of the sample 40 is irradiated with the Co characteristic X-ray and the diffracted X-ray from the first region 66 is detected by the upper half area 62 of the CCD sensor 20. Similarly, the second region 68 which is the lower half of the sample 40 is irradiated with the Cu characteristic X-ray and the diffracted X-ray from the second region 68 is detected by the lower half area 64 of the CCD sensor 20.

Figure 5:
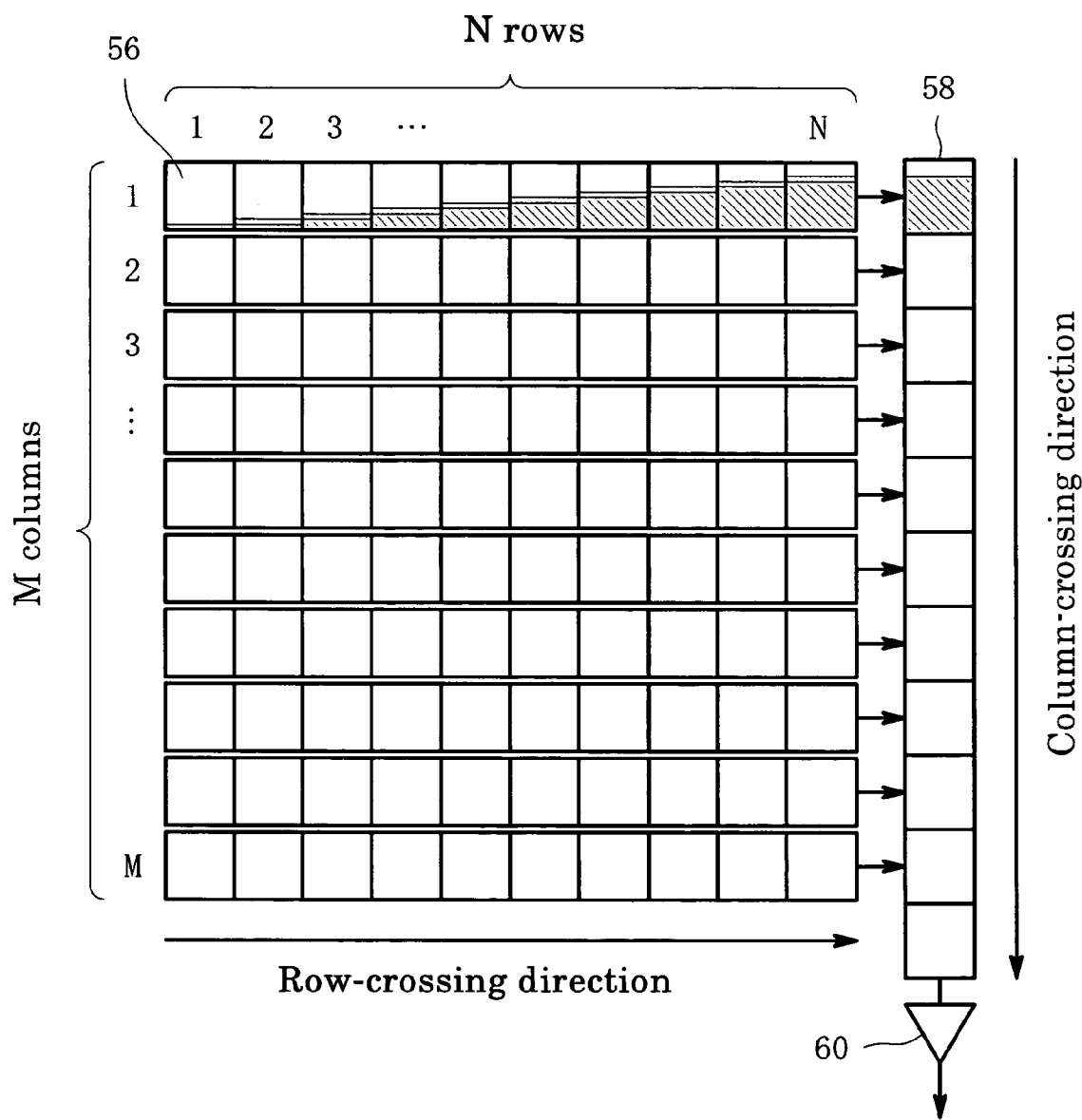
FIG. 5 shows a configuration of a CCD sensor.

FIG. 5 shows a configuration of a CCD sensor which is a full frame transfer (FFT) type CCD sensor capable of executing the TDI operation. The CCD sensor includes N-row times M-column pixels, 512 times 512 pixels in this embodiment. In each column, photo acceptance cells 56 are arranged in line from the first row to the Nth row. Each acceptance cell 56 makes up one pixel and acts as a potential well, i.e., electronic well, for accumulating electric charges. The N acceptance cells from the first row to the Nth row make up an analog-type vertical shift resister. When the acceptance cell 56 receives an X-ray, the acceptance cell 56 generates signal charges which are accumulated in the cell. The accumulated charges are transferred to the next row on every reception of a vertical transfer clock signal. The pulse interval of the vertical transfer clock signal corresponds to the transfer period of the TDI operation. The charges in the last Nth row are transferred to an analog-type horizontal shift resister 58 which is made of potential wells including the first column to the Mth column. The charges in each column of the horizontal shift resister 58 are transferred to the next column on every reception of a horizontal transfer clock signal. The charges in the potential well of the Mth column are converted to an analog voltage signal in the output circuit 60 and the voltage signal is read out.

In the X-ray diffraction apparatus as shown in FIG. 1, when it is intended to record a diffraction pattern under a combination of the 2θ-rotation of the CCD sensor and the TDI operation of the CCD sensor, a specified relationship must be established between the speed of the 2θ-rotation and the transfer frequency of the TDI operation of the CCD sensor. It would be advantageous for establishing the relationship that the control device of the X-ray diffraction apparatus feeds a transfer timing signal, which is based on the speed of the 2θ-rotation, to the CCD sensor. Stating in detail, the control operation is carried out so that the product of the transfer frequency of the TDI operation and the pixel size of the CCD sensor along the charge transfer direction, i.e., row-crossing direction in FIG. 5, coincides with the moving speed of the 2θ-rotation of the CCD sensor. When it is intended to record the diffraction patterns on the CCD sensor which is rotating with the 2θ-rotation, the CCD sensor must be always under the exposure condition during the TDI operation.

FIG. 6 illustrates an arrangement of storage cells in a memory which temporarily stores the measured raw data coming from the output circuit 60 in FIG. 5. The measured raw data is denoted by a symbol S, and the measured raw data in the first column of the first channel is expressed by S(1,1). The measured raw data in the cells ranging from the first column to the Mth column of the first channel, S(1,1), S(1,2), S(1,3), . . . , S(1,M), are stored respectively in the M storage cells in the first channel. Similarly, the data in the second and more other channels are stored in the respective storage cells. The direction along which the channel number increases coincides with the direction along which the diffraction angle 2θ increases. If the thus stored measured raw data in the two-dimensional arrangement are displayed in the display as they are, it would become a two-dimensional image. On the other hand, if the data in the cells ranging from the first column to the Mth column are summed up to obtain one data for one channel such as T(1), T(2), . . . , called as a sum data, the measured data become a one-dimensional result. If displaying the diffraction pattern is desired, a graph should be created with the diffraction angle 2θ in abscissa and the sum data for each channel number corresponding to the angle 2θ in ordinate. Such X-ray diffraction measurement using the TDI-operable two-dimensional CCD sensor is disclosed in detail in the second publication mentioned above.

Figure 7:
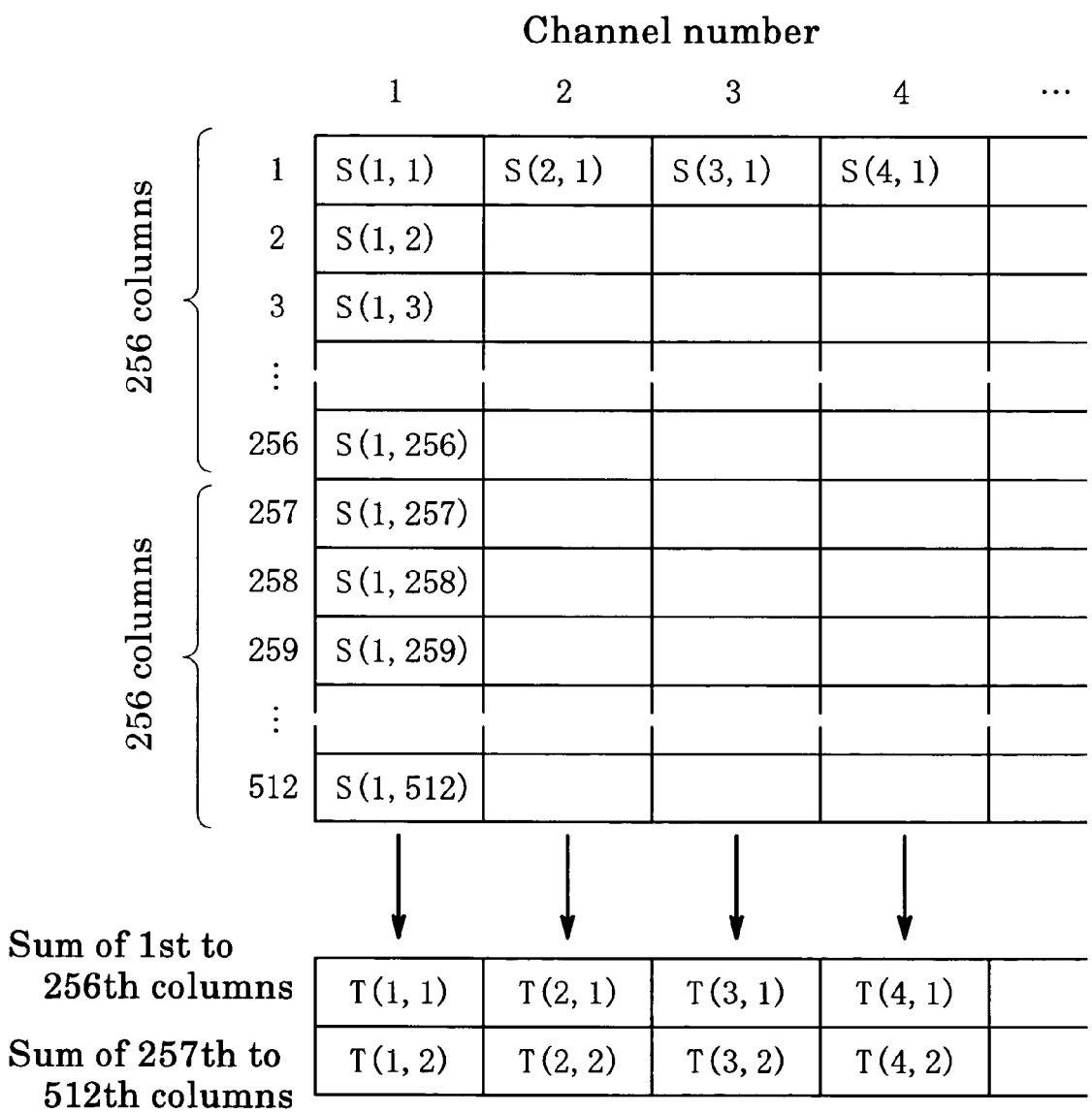
FIG. 7 illustrates an arrangement of the story cells, indicating a summing operation in which 512-row times 512-column pixels are sectioned into upper and lower areas and measured data are summed up in a column-crossing direction separately for each area.

In this embodiment, as shown in FIG. 4, many pixels of the CCD sensor 20 are sectioned vertically into two areas 62 and 64 so that the measured data in the column-crossing direction are summed up separately for each area. FIG. 7 illustrates an arrangement of the story cells, indicating a summing operation in which 512-row times 512-column pixels are sectioned into upper and lower areas and measured data are summed up in a column-crossing direction separately for each area. Explaining the first channel, a sum of the measured raw data ranging from the first column to the 256th column is T(1,1) and another sum of the measured raw data ranging from the 257th column to the 512th column is T(1,2). The sum data T(1,1) regarding the upper half area pixels expresses the diffracted X-ray intensity coming from the Co characteristic X-ray, and the sum data T(1,2) regarding the lower half area pixels expresses the diffracted X-ray intensity coming from the Cu characteristic X-ray. The second and more other channels can be dealt with similarly. Therefore, if a diffraction pattern is displayed based on the measured data of the upper half of the CCD sensor 20, the pattern is the powder diffraction pattern by the Co characteristic X-ray. If a diffraction pattern is displayed based on the measured data of the lower half of the CCD sensor 20, the pattern is the powder diffraction pattern by the Cu characteristic X-ray.

Actually, referring to FIG. 4, some pixels near the boundary between the upper half area 62 of the CCD sensor 20 and the lower half area 64 would receive both the Co and Cu characteristic X-rays which may be mixed with each other to a certain degree, because it is impossible to make the vertical divergence perfectly nothing. Therefore, when summing up in the column-crossing direction as shown in FIG. 7, the measured data in the pixels near the above-mentioned boundary may be excluded from the sum data in the column-crossing direction.

Figure 8:
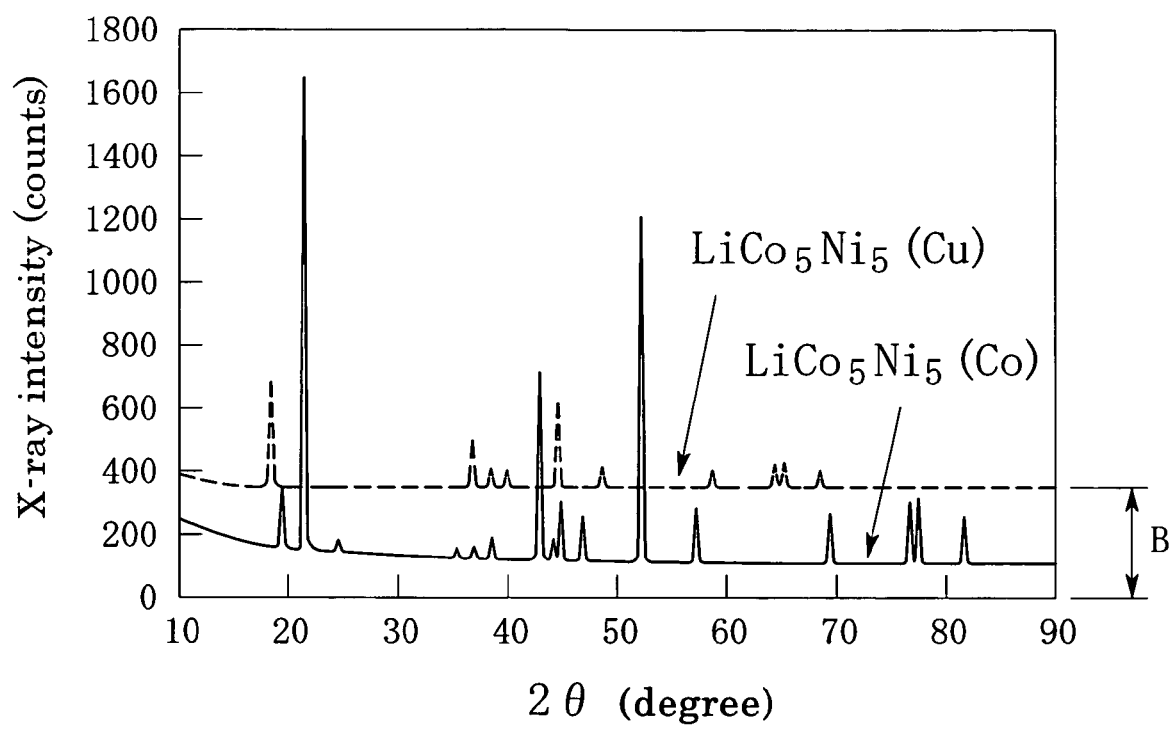
FIG. 8 is a graph of powder diffraction patterns which are measured with the X-ray diffraction apparatus shown in FIG. 1.

FIG. 8 is a graph of powder diffraction patterns of $LiCo_5Ni_5$ powder sample which were measured with the use of the X-ray diffraction apparatus shown in FIG. 1. When a sample includes Co and Ni, the following result will be expected. The energy of the CuKα line (the Cu characteristic X-ray) is 8 keV, the energy of the CoKα line (the Co characteristic X-ray) is 6.9 keV, the energy of the K-absorption edge of Co is 7.7 keV, and the energy of the K-absorption edge of Ni is 8.3 keV. It is expected therefore that, in a sample region which has been irradiated with the CuKα line, Co is excited to generate Co fluorescent X-ray so that the background would increase. On the other hand, it is expected that, in a sample region which has been irradiated with the CoKα line, there occurs no generation of fluorescent X-ray so that there would be obtained diffraction data with reduced background.

Referring to FIG. 8, a pattern denoted by $LiCo_5Ni_5(Co)$ is the powder diffraction pattern by the Co characteristic X-ray, which is obtained based on the measured data in the upper half area of the CCD sensor. The other pattern denoted by $LiCo_5Ni_5(Cu)$ is the powder diffraction pattern by the Cu characteristic X-ray, which is obtained based on the measured data in the lower half area of the CCD sensor. The measurement condition is 40 kV, 200 mA in X-ray tube operation and 40 degrees per minute in 2θ scanning speed.

In the graph shown in FIG. 8, the diffraction pattern of $LiCo_5Ni_5(Cu)$ has a larger background B as compared with the $LiCo_5Ni_5(Co)$ pattern. The greater part of the background B would be a fluorescent X-ray which has been detected with the reason that Co in the sample is exited by the Cu characteristic X-ray to generate the fluorescent X-ray.

It is possible, with this embodiment, to collect X-ray diffraction data using two kinds of characteristic X-rays at the same time (i.e., under perfectly the same condition) in one operation of measurement, so that there are improved an analysis ability, an analysis accuracy and analysis reliability in qualitative and quantitative analyses. For a sample including Co and Ni like the measured sample, since the energy of the Co absorption edge resides between the energy of the CoKα line and the energy of the CuKα line, it becomes possible to carry out an analysis using the Co abnormal dispersion.

The present invention is not limited to the embodiments mentioned above, but is applicable to the following modifications.

(1) Characteristic X-rays of three or more kinds of materials may be used. For example, referring to FIG. 3, Mo (molybdenum) may be used in addition to Co and Cu. In such a case, the three materials Mo, Co and Cu may be arranged to be sectioned vertically.

(2) The Soller slit may be replaced by another divergence angle restriction device to restrict the longitudinal divergence. For example, a monochromator may be arranged instead of the Soller slit to make an X-ray monochromatic and collimated, so that the longitudinal divergence is remarkably reduced. In such a case, a monochromator must be divided into a monochromator part for the Co characteristic X-ray and another monochromator part for the Cu characteristic X-ray.

(3) The TDI-operable two-dimensional CCD sensor may be replaced by any one-dimensional or two-dimensional X-ray detector which is position sensitive at least vertically. Since the sensor is, in principle, not necessarily position sensitive in the 2θ direction in carrying out the present invention, a sensor which is position sensitive only vertically is sufficient. In such a case, the sensor may have many pixels in the vertical direction, or may have only two detection areas sectioned to match two kinds of characteristic X-rays so as to be position sensitive.

What is claimed is:
1. An X-ray diffraction apparatus comprising:
   (a) an X-ray tube including an anode having a first target region made of a first material and a second target region made of a second material which is different from the first material, wherein the first target region and the second target region are sectioned in a Z-direction perpendicular to an X-ray take-off direction;
   (b) a sample holder for holding a sample so as to be simultaneously irradiated with a first characteristic X-ray emitted from the first target region and a second characteristic X-ray emitted from the second target region;
   (c) an incident-side Z-direction-divergence restriction device which is arranged between the X-ray tube and the sample to restrict X-ray divergence in the Z-direction;
   (d) an X-ray detector for detecting a diffracted X-ray coming from the sample, wherein the X-ray detector is position sensitive at least in the Z-direction and detects separately a diffracted X-ray coming from a first region of the sample which is irradiated with the first characteristic X-ray and another diffracted X-ray coming from a second region of the sample which is irradiated with the second characteristic X-ray; and
   (e) a receiving-side Z-direction-divergence restriction device which is arranged between the sample and the X-ray detector to restrict X-ray divergence in the Z-direction.

2. An X-ray diffraction apparatus according to claim 1, wherein the X-ray detector comprises one of a one-dimensional CCD sensor and a two dimensional CCD sensor.

3. An X-ray diffraction apparatus according to claim 1, wherein the X-ray detector comprises a two-dimensional CCD sensor and executes a TDI operation.

4. An X-ray diffraction apparatus according to claim 3, wherein both the incident-side Z-direction-divergence restriction device and the receiving-side Z-direction-divergence restriction device are Soller slits.

5. An X-ray diffraction apparatus according to claim 1, wherein both the incident-side Z-direction-divergence restriction device and the receiving-side Z-direction-divergence restriction device are Soller slits.

* * * * *